United States Patent
Bishop et al.

(10) Patent No.: US 11,452,734 B2
(45) Date of Patent: *Sep. 27, 2022

(54) METHOD OF TREATING AND PREVENTING SECONDARY HYPERPARATHYROIDISM

(71) Applicants: OPKO IRELAND GLOBAL HOLDINGS, LTD., Grand Cayman (KY); OPKO RENAL, LLC, Miami, FL (US)

(72) Inventors: Charles W. Bishop, Miami Beach, FL (US); Keith H. Crawford, Parker, CO (US); Eric J. Messner, Lake Forest, IL (US); P. Martin Petkovich, Kingston (CA); Christian F. Helvig, Markham (CA)

(73) Assignee: EIRGEN PHARMA LTD., Waterford (IE)

( * ) Notice: Subject to any disclaimer, the term of this patent is extended or adjusted under 35 U.S.C. 154(b) by 5 days.

This patent is subject to a terminal disclaimer.

(21) Appl. No.: 16/858,395

(22) Filed: Apr. 24, 2020

(65) Prior Publication Data

US 2020/0253987 A1    Aug. 13, 2020

Related U.S. Application Data

(60) Continuation of application No. 15/918,620, filed on Mar. 12, 2018, which is a division of application No. 15/220,963, filed on Jul. 27, 2016, now Pat. No. 9,913,852, which is a continuation of application No. 13/680,997, filed on Nov. 19, 2012, now Pat. No. 9,402,855, which is a continuation of application No. 12/305,572, filed as application No. PCT/US2007/071791 on Jun. 21, 2007, now Pat. No. 8,329,677.

(60) Provisional application No. 60/815,148, filed on Jun. 21, 2006.

(51) Int. Cl.
| | |
|---|---|
| *A61K 31/593* | (2006.01) |
| *A61K 31/59* | (2006.01) |
| *A61K 31/592* | (2006.01) |
| *A61K 9/48* | (2006.01) |
| *A61P 5/18* | (2006.01) |
| *A61K 9/00* | (2006.01) |

(52) U.S. Cl.
CPC .......... *A61K 31/593* (2013.01); *A61K 9/0053* (2013.01); *A61K 9/48* (2013.01); *A61K 9/4825* (2013.01); *A61K 31/59* (2013.01); *A61K 31/592* (2013.01); *A61P 5/18* (2018.01)

(58) Field of Classification Search
CPC ..... A61K 31/593; A61K 31/59; A61K 31/592
See application file for complete search history.

(56) References Cited

U.S. PATENT DOCUMENTS 6,521,608 B1 * 2/2003 Henner .................. A61P 35/02
514/167

* cited by examiner

*Primary Examiner* — San Ming R Hui
(74) *Attorney, Agent, or Firm* — Michael Muczynski

(57) ABSTRACT

The method of treating elevated blood levels of iPTH by increasing or maintaining blood concentrations of both 25-hydroxyvitamin D and 1,25-dihydroxyvitamin D in a patient by administering, as necessary, both Vitamin D repletion and Vitamin D hormone replacement therapies, is disclosed. The blood concentrations of 25-hydroxyvitamin D are increased to and maintained at or above 30 ng/mL, and blood concentrations of 1,25-dihydroxyvitamin D are increased to or maintained within a patient's normal historical physiological range for 1,25-dihydroxyvitamin D without causing substantially increased risk of hypercalcemia, hyperphosphatemia or over suppression of plasma iPTH in the patient. The blood levels of 25-hydroxyvitamin D are maintained at or above 30 ng/mL between doses of Vitamin D repletion therapies, and the blood levels of 1,25-dihydroxyvitamin D are maintained in the patient's normal historical physiological range between doses of Vitamin D hormone replacement therapies. In one aspect, the disclosure includes methods wherein the blood concentration of 25-hydroxyvitamin D during treatment comprises predominantly 25-hydroxyvitamin $D_3$, and/or wherein the method includes administering predominantly or solely 25-hydroxyvitamin $D_3$ for 25-hydroxyvitamin D repletion and/or maintenance.

20 Claims, No Drawings

METHOD OF TREATING AND PREVENTING SECONDARY HYPERPARATHYROIDISM

This is a continuation of U.S. patent application Ser. No. 15/918,620 filed Mar. 12, 2018, which is a division of U.S. patent application Ser. No. 15/220,963 filed Jul. 27, 2016, which is a continuation of U.S. patent application Ser. No. 13/680,997 filed Nov. 19, 2012 (now U.S. Pat. No. 9,402,855), which is a continuation of U.S. patent application Ser. No. 12/305,572 filed Mar. 2, 2009 (now U.S. Pat. No. 8,329,677), which is the National Phase of International Application No. PCT/US2007/071791 filed Jun. 21, 2007, and which claims the benefit of priority under 35 U.S.C. § 119(e) of U.S. Provisional Patent Application Ser. No. 60/815,148 filed Jun. 21, 2006. The disclosure of each priority application is incorporated herein by reference.

BACKGROUND

Field of the Disclosure

The disclosure relates generally to Vitamin D repletion and active Vitamin D hormone replacement. More particularly, the disclosure relates to methods of treating elevated blood levels of intact parathyroid hormone (iPTH), such as in secondary hyperparathyroidism, by increasing or maintaining blood concentrations of both 25-hydroxyvitamin D and 1,25-dihydroxyvitamin D in a patient by administering, as necessary, both Vitamin D repletion and Vitamin D hormone replacement therapies.

Brief Description of Related Technology

Secondary hyperparathyroidism is a disorder which develops primarily because of Vitamin D deficiency. It is characterized by abnormally elevated blood levels of parathyroid hormone (PTH) and, in the absence of early detection and treatment, it becomes associated with parathyroid gland hyperplasia and a constellation of metabolic bone diseases. It is a common complication of chronic kidney disease (CKD), with rising incidence as CKD progresses. Secondary hyperparathyroidism can also develop in individuals with healthy kidneys, due to environmental, cultural or dietary factors which prevent adequate Vitamin D supply.

"Vitamin D" is a term that refers broadly to the organic substances named Vitamin $D_2$, Vitamin $D_3$, Vitamin $D_4$, etc., and to their metabolites and hormonal forms that influence calcium and phosphorus homeostasis. "Vitamin D deficiency" is a term that broadly refers to reduced or low blood levels of Vitamin D, as defined immediately above.

The most widely recognized forms of Vitamin D are Vitamin $D_2$ (ergocalciferol) and Vitamin $D_3$ (cholecalciferol). Vitamin $D_2$ is produced in plants from ergosterol during sunlight exposure and is present, to a limited extent, in the human diet. Vitamin $D_3$ is generated from 7-dehydrocholesterol in human skin during exposure to sunlight and also is found, to a greater extent than Vitamin $D_2$, in the human diet, principally in dairy products (milk and butter), certain fish and fish oils, and egg yolk. Vitamin D supplements for human use consist of either Vitamin $D_2$ or Vitamin $D_3$.

Both Vitamin $D_2$ and Vitamin $D_3$ are metabolized into prohormones by one or more enzymes located in the liver. The involved enzymes are mitochondrial and microsomal cytochrome P450 (CYP) isoforms, including CYP27A1, CYP2R1, CYP3A4, CYP2J3 and possibly others. These enzymes metabolize Vitamin $D_2$ into two prohormones known as 25-hydroxyvitamin $D_2$ and 24(S)-hydroxyvitamin $D_2$, and Vitamin $D_3$ into a prohormone known as 25-hydroxyvitamin $D_3$. The two 25-hydroxylated prohormones are more prominent in the blood, and are collectively referred to as "25-hydroxyvitamin D". Vitamin $D_2$ and Vitamin $D_3$ can be metabolized into these same prohormones outside of the liver in certain epithelial cells, such as enterocytes, which contain the same (or similar) enzymes, but extrahepatic prohormone production probably contributes little to blood levels of 25-hydroxyvitamin D.

The rates of hepatic and extrahepatic production of the Vitamin D prohormones are not tightly regulated, and they vary mainly with intracellular concentrations of the precursors (Vitamin $D_2$ and Vitamin $D_3$). Higher concentrations of either precursor increase prohormone production, while lower concentrations decrease production. Hepatic production of prohormones is inhibited by high levels of 25-hydroxyvitamin D via a poorly understood mechanism apparently directed to prevention of excessive blood prohormone levels.

The Vitamin D prohormones are further metabolized in the kidneys into potent hormones by an enzyme known as CYP27B1 (or 25-hydroxyvitamin $D_3$-1α-hydroxylase) located in the proximal kidney tubule. The prohormones 25-hydroxyvitamin $D_2$ and 24(S)-hydroxyvitamin $D_2$ are metabolized into hormones known as 1α,25-dihydroxyvitamin $D_2$ and 1α,24(S)-dihydroxyvitamin $D_2$. Likewise, 25-hydroxyvitamin $D_3$ is metabolized into a hormone known as 1α,25-dihydroxyvitamin $D_3$ (or calcitriol). These hormones are released by the kidneys into the blood for systemic delivery. The two 25-hydroxylated hormones, usually far more prominent in the blood than 1α,24(S)-dihydroxyvitamin $D_2$, are collectively referred to as "1,25-dihydroxyvitamin D". Vitamin D prohormones can be metabolized into hormones outside of the kidneys in keratinocytes, lung epithelial cells, enterocytes, cells of the immune system (e.g., macrophages) and certain other cells containing CYP27B1 or similar enzymes, but such extrarenal hormone production is incapable of sustaining normal blood levels of 1,25-dihydroxyvitamin D in advanced CKD.

Blood levels of 1,25-dihydroxyvitamin D are precisely regulated by a feedback mechanism which involves PTH. The renal 1α-hydroxylase (or CYP27B1) is stimulated by PTH and inhibited by 1,25-dihydroxyvitamin D. When blood levels of 1,25-dihydroxyvitamin D fall, the parathyroid glands sense this change via intracellular Vitamin D receptors (VDR) and secrete PTH. The secreted PTH stimulates expression of renal CYP27B1 and, thereby, increases production of Vitamin D hormones. As blood concentrations of 1,25-dihydroxyvitamin D rise again, the parathyroid glands attenuate further PTH secretion. As blood PTH levels fall, renal production of Vitamin D hormones decreases. Rising blood levels of 1,25-dihydroxyvitamin D also directly inhibit further Vitamin D hormone production by CYP27B1. PTH secretion can be abnormally suppressed in situations where blood 1,25-dihydroxyvitamin D concentrations become excessively elevated, as can occur in certain disorders or as a result of bolus doses of Vitamin D hormone replacement therapies. Oversuppression of PTH secretion can cause or exacerbate disturbances in calcium homeostasis. The parathyroid glands and the renal CYP27B1 are so sensitive to changes in blood concentrations of Vitamin D hormones that serum 1,25-dihydroxyvitamin D is tightly controlled, fluctuating up or down by less than 20% during any 24-hour period. In contrast to renal production of Vitamin D hormones, extrarenal production is not under precise feedback control.

The Vitamin D hormones have essential roles in human health which are mediated by the intracellular VDR. In particular, the Vitamin D hormones regulate blood calcium levels by controlling intestinal absorption of dietary calcium and reabsorption of calcium by the kidneys. The Vitamin D hormones also participate in the regulation of cellular differentiation and growth and normal bone formation and metabolism. Further, Vitamin D hormones are required for the normal functioning of the musculoskeletal, immune and renin-angiotensin systems. Numerous other roles for Vitamin D hormones are being postulated and elucidated, based on the documented presence of intracellular VDR in nearly every human tissue.

The actions of Vitamin D hormones on specific tissues depend on the degree to which they bind to (or occupy) the intracellular VDR in those tissues. The three Vitamin D hormones $1\alpha,25$-dihydroxyvitamin $D_2$, $1\alpha,24(S)$-dihydroxyvitamin $D_2$, and $1\alpha,25$-dihydroxyvitamin $D_3$ have nearly identical affinities for the VDR and, therefore, have essentially equivalent VDR binding when present at the same intracellular concentrations. VDR binding increases as the intracellular concentrations of the hormones rise, and decreases as the intracellular concentrations fall. In all cells, intracellular concentrations of the Vitamin D hormones change in direct proportion to changes in blood hormone concentrations. In cells containing CYP27B1 (or similar enzymes), intracellular concentrations of the Vitamin D hormones also change in direct proportion to changes in blood and/or intracellular prohormone concentrations, as discussed above.

Vitamin $D_2$, Vitamin $D_3$ and their prohormonal forms have affinities for the VDR which are estimated to be at least 100-fold lower than those of the Vitamin D hormones. As a consequence, physiological concentrations of these hormone precursors exert little, if any, biological actions without prior metabolism to Vitamin D hormones. However, supraphysiological levels of these hormone precursors, especially the prohormones, in the range of 10 to 1,000 fold higher than normal, can sufficiently occupy the VDR and exert actions like the Vitamin D hormones.

Blood levels of Vitamin $D_2$ and Vitamin $D_3$ are normally present at stable, concentrations in human blood, given a sustained, adequate supply of Vitamin D from sunlight exposure and an unsupplemented diet. Slight, if any, increases in blood Vitamin D levels occur after meals since unsupplemented diets have low Vitamin D content, even those containing foods fortified with Vitamin D. The Vitamin D content of the human diet is so low that the National Institutes of Health (NIH) cautions "it can be difficult to obtain enough Vitamin D from natural food sources" [NIH, Office of Dietary Supplements, Dietary Supplement Fact Sheet: Vitamin D (2005)]. Almost all human Vitamin D supply comes from fortified foods, exposure to sunlight or from dietary supplements, with the last source becoming increasingly important. Blood Vitamin D levels rise only gradually, if at all, after sunlight exposure since cutaneous 7-dehydrocholesterol is modified by UV radiation to pre-Vitamin $D_3$ which undergoes thermal conversion in the skin to Vitamin $D_3$ over a period of several days before circulating in the blood.

Blood Vitamin D hormone concentrations also remain generally constant through the day in healthy individuals, but can vary significantly over longer periods of time in response to seasonal changes in sunlight exposure or sustained alterations in Vitamin D intake. Marked differences in normal Vitamin D hormone levels are commonly observed between healthy individuals, with some individuals having stable concentrations as low as approximately 20 pg/mL and others as high as approximately 70 pg/mL. Due to this wide normal range, medical professionals have difficulty interpreting isolated laboratory determinations of serum total 1,25-dihydroxyvitamin D; a value of 25 pg/mL may represent a normal value for one individual or a relative deficiency in another.

Transiently low blood levels of 1,25-dihydroxyvitamin D stimulate the parathyroid glands to secrete PTH for brief periods ending when normal blood Vitamin D hormone levels are restored. In contrast, chronically low blood levels of 1,25-dihydroxyvitamin D continuously stimulate the parathyroid glands to secrete PTH, resulting in a disorder known as secondary hyperparathyroidism. Chronically low hormone levels also decrease intestinal calcium absorption, leading to reduced blood calcium concentrations (hypocalcemia) which further stimulate PTH secretion. Continuously stimulated parathyroid glands become increasingly hyperplastic and eventually develop resistance to regulation by vitamin D hormones. Without early detection and treatment, secondary hyperparathyroidism progressively increases in severity, causing debilitating metabolic bone diseases, including osteoporosis and renal osteodystrophy.

Chronically low blood levels of 1,25-dihydroxyvitamin D develop when there is insufficient renal CYP27B1 to produce the required supply of Vitamin D hormones, a situation which commonly arises in CKD. The activity of renal CYP27B1 declines as glomerular filtration rate (GFR) falls below approximately 60 ml/min/1.73 $m^2$ due to the loss of functioning nephrons. In end-stage renal disease (ESRD), when the kidneys fail completely and hemodialysis is required for survival, renal CYP27B1 often becomes altogether absent. Any remaining CYP27B1 is greatly inhibited by elevated serum phosphorous (hyperphosphatemia) caused by inadequate renal excretion of dietary phosphorous.

Chronically low blood levels of 1,25-dihydroxyvitamin D also develop because of a deficiency of Vitamin D prohormones, since renal hormone production cannot proceed without the required precursors. Prohormone production declines markedly when cholecalciferol and ergocalciferol are in short supply, a condition often described by terms such as "Vitamin D insufficiency", "Vitamin D deficiency" or "hypovitaminosis D." Therefore, measurement of 25-hydroxyvitamin D levels in blood has become the accepted method among healthcare professionals to monitor Vitamin D status. Recent studies have documented that the great majority of CKD patients have low blood levels of 25-hydroxyvitamin D, and that the prevalence of Vitamin D insufficiency and deficiency increases as CKD progresses.

It follows that individuals most vulnerable to developing chronically low blood levels of 1,25-dihydroxyvitamin D are those with CKD. Most CKD patients typically have decreased levels of renal CYP27B1 and a shortage of 25-hydroxyvitamin D prohormones. Not surprisingly, most CKD patients develop secondary hyperparathyroidism. Unfortunately, early detection and treatment of secondary hyperparathyroidism in CKD is rare, let alone prevention.

The National Kidney Foundation (NKF) has recently focused the medical community's attention on the need for early detection and treatment of secondary hyperparathyroidism by publishing Kidney Disease Outcomes Quality Initiative (K/DOQI) Clinical Practice Guidelines for Bone Metabolism and Disease in Chronic Kidney Disease [Am. J. Kidney Dis. 42:S1-S202, 2003)]. The K/DOQI Guidelines identified the primary etiology of secondary hyperparathyroidism as chronically low blood levels of 1,25-dihydroxyvitamin and recommended regular screening in CKD Stages 3 through 5 for elevated blood PTH levels relative to stage-specific PTH target ranges. CKD Stage 3 was defined as moderately decreased kidney function (GFR of 30-59 mL/min/1.73 m$^2$) with an intact PTH (iPTH) target range of 30-70 pg/mL; Stage 4 was defined as severely decreased kidney function (GFR of 15-29 mL/min/1.73 m$^2$), with an iPTH target range of 70-110 pg/mL; and Stage 5 was defined as kidney failure (GFR of <15 mL/min/1.73 m$^2$ or dialysis) with an iPTH target range of 150-300 pg/mL. In the event that screening revealed an iPTH value to be above the target range for the stage of CKD (Stage 3 or 4), the Guidelines recommended a follow-up evaluation of serum total 25-hydroxyvitamin D to detect possible Vitamin D insufficiency or deficiency. If 25-hydroxyvitamin D below 30 ng/mL was observed, the recommended intervention was Vitamin D repletion therapy using orally administered ergocalciferol. If 25-hydroxyvitamin D above 30 ng/mL was observed, the recommended intervention was Vitamin D hormone replacement therapy using oral or intravenous Vitamin D hormones or analogues. The Guidelines did not recommend the concurrent application of Vitamin D repletion and Vitamin D hormone replacement therapies, consistent with warnings mandated by the Food and Drug Administration in package inserts for Vitamin D hormone replacement products.

The NKF K/DOQI Guidelines defined Vitamin D sufficiency as serum 25-hydroxyvitamin D levels ≥30 ng/mL. Recommended Vitamin D repletion therapy for patients with "Vitamin D insufficiency", defined as serum 25-hydroxyvitamin D of 16-30 ng/mL, was 50,000 IU per month of oral Vitamin $D_2$ for 6 months, given either in single monthly doses or in divided doses of approximately 1,600 IU per day. Recommended repletion therapy for patients with "Vitamin D deficiency" was more aggressive: for "mild" deficiency, defined as serum 25-hydroxyvitamin D of 5-15 ng/mL, the Guidelines recommended 50,000 IU per week of oral Vitamin $D_2$ for 4 weeks, followed by 50,000 IU per month for another 5 months; for "severe" deficiency, defined as serum 25-hydroxyvitamin D below 5 ng/mL, the Guidelines recommended 50,000 IU/week of oral Vitamin $D_2$ for 12 weeks, followed by 50,000 IU/month for another 3 months. Doses of 50,000 IU per week are approximately equivalent to 7,000 IU per day.

The K/DOQI Guidelines recommended currently available oral Vitamin D products, especially those containing Vitamin $D_2$, for achieving and maintaining optimal blood 25-hydroxyvitamin D levels. Unfortunately, these preparations are far from ideal for use in CKD patients, and can be altogether ineffective based on recently published clinical investigations. They typically contain 400 IU to 5,000 IU of Vitamin $D_3$ or 50,000 IU of Vitamin $D_2$ and are formulated for quick or immediate release in the gastrointestinal tract. When administered at chronically high doses, as is usually required for repletion, these products have significant and, often, severe limitations. They produce pharmacological concentrations of Vitamin D in the lumen of the duodenum which promote catabolism of Vitamin D by 26-hydroxylation in the local enterocytes, causing decreased systemic bioavailability and supraphysiological surges in blood Vitamin D levels. Such surges are undesirable because they promote storage of Vitamin D in adipose tissue, which is less available for later hepatic conversion to 25-hydroxyvitamin D, and hepatic catabolism of Vitamin D. Further, they cause abrupt increases in blood and intracellular 25-hydroxyvitamin D levels, thereby promoting marked catabolism of both Vitamin D and 25-hydroxyvitamin D by 24- and/or 26-hydroxylation in the kidney and other tissues, down-regulation of hepatic production of Vitamin D prohormones, unnecessarily impeding the efficient repletion of Vitamin D insufficiency or deficiency, and local aberrations in calcium and phosphorus homeostasis mediated by direct binding to VDR.

All but two FDA-approved "quick-release" high unit dose (50,000 IU) prescription formulations of Vitamin $D_2$, considered by the NKF Clinical Practice Guidelines to be potentially safer than Vitamin $D_3$, have been discontinued from the U.S. market because of poor acceptance by healthcare professionals. Administration of 25-hydroxyvitamin $D_3$ in an immediate release oral formulation has been tried as an alternative method of Vitamin D supplementation. This approach, which has been subsequently abandoned, caused problems as do the currently used Vitamin D supplements. Specifically, administration of 25-hydroxyvitamin $D_3$ produced surges or spikes in blood and intracellular 25-hydroxyvitamin D levels, thereby promoting (a) competitive displacement of Vitamin D hormones from the serum Vitamin D Binding Protein (DBP) and excessive delivery of the displaced hormones to tissues containing VDR, and (b) transiently excessive renal and extrarenal production of Vitamin D hormones, which together led to local and systemic aberrations in calcium and phosphorus metabolism. In addition, these surges in blood 25-hydroxyvitamin D levels promoted catabolism of both Vitamin D and 25-hydroxyvitamin D by 24- and/or 26-hydroxylation in the kidney and other tissues, down-regulation of hepatic production of Vitamin D prohormones, unnecessarily impeding the efficient repletion of Vitamin D insufficiency or deficiency, and, additional local aberrations in calcium and phosphorus homeostasis mediated by direct binding to VDR. Importantly, immediate release 25-hydroxyvitamin $D_3$ promoted its intestinal absorption via a mechanism substantially involving transport to the liver in chylomicrons, rather than bound to the serum DBP. Delivery of 25-hydroxyvitamin D to the liver via chylomicrons significantly increases the likelihood of its catabolism.

Clearly, a novel alternative approach to Vitamin D therapy is sorely needed, given the problems encountered with the currently available oral Vitamin D supplements and with previously used oral 25-hydroxyvitamin $D_3$. Given such an alternative approach, which is described herein, it becomes possible, for the first time, to concurrently apply Vitamin D repletion and Vitamin D hormone replacement therapies in CKD patients who have need of both types of therapies to effectively treat and subsequently prevent secondary hyperparathyroidism.

SUMMARY

In one aspect, the present invention provides a method of increasing or maintaining blood concentrations of both 25-hydroxyvitamin D and 1,25-dihydroxyvitamin D in a patient by administering, as necessary, both Vitamin D repletion and active Vitamin D hormone replacement therapies. The blood concentrations of 25-hydroxyvitamin D are increased to and maintained at or above 30 ng/mL, and blood concentrations of 1,25-dihydroxyvitamin D are increased to or maintained within a patient's normal historical physiological range for 1,25-dihydroxyvitamin D without causing substantially increased risk of hypercalcemia, hyperphosphatemia or over suppression of plasma iPTH in the patient. The blood levels of 25-hydroxyvitamin D are maintained at or above 30 ng/mL between doses of Vitamin D repletion therapies, and the blood levels of 1,25-dihydroxyvitamin D are maintained in the patient's normal historical physiological range between doses of Vitamin D hormone replacement therapies. In one preferred embodiment, the blood concentration of 25-hydroxyvitamin D during treatment comprises predominantly 25-hydroxyvitamin $D_3$, with a lesser amount of 25-hydroxyvitamin $D_2$. In another preferred embodiment, the method includes administering predominantly 25-hydroxyvitamin $D_3$, with a lesser amount of 25-hydroxyvitamin $D_2$, or solely 25-hydroxyvitamin $D_3$, for 25-hydroxyvitamin D repletion and/or maintenance.

In another aspect, the invention provides a method of concurrently lowering or maintaining plasma iPTH levels, increasing or maintaining serum calcium levels, maintaining serum phosphorous levels, increasing or maintaining serum 25-hydroxyvitamin D, and increasing or maintaining serum 1,25-dihydroxyvitamin D levels in a human patient by administering to the patient, as necessary, both Vitamin D repletion and Vitamin D hormone replacement therapies. The method can further include administration, as necessary, of phosphate binders and/or calcimimetic agents. In one preferred embodiment, the blood concentration of 25-hydroxyvitamin D during treatment comprises predominantly 25-hydroxyvitamin $D_3$, with a lesser amount of 25-hydroxyvitamin $D_2$. In another preferred embodiment, the method includes administering predominantly 25-hydroxyvitamin $D_3$, with a lesser amount of 25-hydroxyvitamin $D_2$, or solely 25-hydroxyvitamin $D_3$, for 25-hydroxyvitamin D repletion and/or maintenance.

In yet another aspect, the invention provides a method of reducing the risk of over suppression of plasma iPTH levels in a patient undergoing treatment for elevated levels of plasma iPTH, by administering, as necessary, both Vitamin D repletion and Vitamin D hormone replacement therapies in amounts sufficient to decrease elevated plasma iPTH levels while avoiding an abnormally low bone turnover rate. In one preferred embodiment, the blood concentration of 25-hydroxyvitamin D during treatment comprises predominantly 25-hydroxyvitamin $D_3$, with a lesser amount of 25-hydroxyvitamin $D_2$. In another preferred embodiment, the method includes administering predominantly 25-hydroxyvitamin $D_3$, with a lesser amount of 25-hydroxyvitamin $D_2$, or solely 25-hydroxyvitamin $D_3$, for 25-hydroxyvitamin D repletion and/or maintenance.

Another aspect of the invention is the use of at least one 25-hydroxyvitamin D and at least one active Vitamin D hormone for the preparation of a medicament for the treatment of a condition described herein, such as secondary hyperparathyroidism. In one preferred embodiment of such a use, the 25-hydroxyvitamin D comprises predominantly 25-hydroxyvitamin $D_3$, with a lesser amount of 25-hydroxyvitamin $D_2$.

Another aspect of the invention is a kit for treatment of a condition described herein, such as secondary hyperparathyroidism, including a 25-hydroxyvitamin D compound, or an active Vitamin D hormone, or combinations thereof, and written instructions for co-treatment with a 25-hydroxyvitamin D compound and an active Vitamin D hormone.

Optionally excluded from the methods of the invention are therapeutic treatment of subjects suffering from renal osteodystrophy (including osteomalacia and osteitis fibrosa cystica).

A fuller appreciation of the specific attributes of this invention will be gained upon an examination of the following detailed description of preferred embodiments, and the appended claim. Before the embodiments of the invention are explained in detail, it is to be understood that the invention is not limited in its application to the details of construction and the arrangements of the components set forth in the following description. The invention is capable of other embodiments and of being practiced or being carried out in various ways. Also, it is understood that the phraseology and terminology used herein are for the purpose of description and should not be regarded as limiting. The use of "including", "having" and "comprising" and variations thereof herein is meant to encompass the items listed thereafter and equivalents thereof as well as additional items and equivalents thereof.

DETAILED DESCRIPTION

The present invention relates to treating and preventing secondary hyperparathyroidism and the underlying chronically low blood levels of 1,25-dihydroxyvitamin D, and various other related abnormalities in mineral and bone metabolism, by administering effective amounts, as necessary, of both Vitamin D repletion and Vitamin D hormone replacement therapies.

In one aspect the present invention provides a method of increasing and then maintaining blood concentrations of 25-hydroxyvitamin D at or above 30 ng/mL, and blood concentrations of 1,25-dihydroxyvitamin D to within a patient's normal historical physiological range for 1,25-dihydroxyvitamin D. As noted hereinbefore, many conditions can lead to chronically low blood levels of 1,25-dihydroxyvitamin D, including CKD (e.g., Stages 3 and 4, and Stage 5), living in northern latitudes and insufficient intake of cholecalciferol and/or ergocalciferol. It has been found that treatment, as needed, with both Vitamin D repletion and Vitamin D hormone replacement therapies of those patients in need thereof can provide blood concentrations of 25-hydroxyvitamin D at or above 30 ng/mL and blood concentrations of 1,25-dihydroxyvitamin D within the patient's normal historical physiological range. One or both of the Vitamin D repletion and Vitamin D hormone replacement therapies, and preferably both, are preferably administered in a manner to avoid bolus surges of Vitamin D in the intestinal lumen or in the blood, thereby avoiding substantially increased risk of hypercalcemia, hyperphosphatemia or over suppression of plasma iPTH in the patient, all of which have been recognized as risks when treatment with a vitamin D therapy is undertaken. Moreover, blood levels of 25-hydroxyvitamin D are maintained above 30 ng/mL and blood levels of 1,25-dihydroxyvitamin D are maintained in the patient's historical physiological range between therapeutic doses. In one preferred embodiment, the blood concentration of 25-hydroxyvitamin D comprises predominantly 25-hydroxyvitamin $D_3$. In another preferred embodiment, the method includes administering predominantly or solely 25-hydroxyvitamin $D_3$ for 25-hydroxyvitamin D repletion and/or maintenance.

In another aspect, the invention provides a method of concurrently lowering or maintaining plasma iPTH levels, increasing or maintaining serum calcium levels, maintaining serum phosphorous levels, increasing or maintaining serum 25-hydroxyvitamin D levels, and increasing or maintaining serum 1,25-dihydroxyvitamin D levels in a human patient by administering to the patient, as needed, effective amounts of both Vitamin D repletion and Vitamin D hormone replacement therapies. Many diseases manifest abnormal levels of more than one hormone and mineral. In CKD, for example, patients may experience decreases in serum total 1,25-dihydroxyvitamin D, increases in plasma iPTH, decreases in serum calcium and increases in serum phosphorous. Treatment in accordance with the present invention presents concurrent leveling and/or maintaining of these various hormone and mineral levels. In one preferred embodiment, the blood concentration of 25-hydroxyvitamin D comprises predominantly 25-hydroxyvitamin $D_3$. In another preferred embodiment, the method includes administering predominantly or solely 25-hydroxyvitamin $D_3$ for 25-hydroxyvitamin D repletion and/or maintenance. Treatment of patients having Stage 3 or 4 CKD, or Stage 5 CKD, is particularly contemplated.

The subject's PTH levels preferably are lowered by at least 30%, or alternatively to the target range for the CKD stage (e.g., for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1)).

Another aspect of the invention is a kit for treatment of a condition described herein, such as Vitamin D deficiency or secondary hyperparathyroidism, including a 25-hydroxyvitamin D compound, or an active Vitamin D hormone, or combinations thereof, and written instructions for co-treatment with a 25-hydroxyvitamin D compound and an active Vitamin D hormone. For example, the kit can include a 25-hydroxyvitamin D compound, such as 25-hydroxyvitamin $D_3$, and written instructions for co-treatment of a subject with the 25-hydroxyvitamin D compound and an active Vitamin D hormone, such as 1,25-dihydroxyvitamin $D_2$. As another example, the kit can include an active Vitamin D hormone and written instructions for co-treatment of a subject with the active Vitamin D hormone and a 25-hydroxyvitamin D compound. As still another example, the kit can include both a 25-hydroxyvitamin D compound and an active Vitamin D hormone, and written instructions for co-treatment of a subject with the 25-hydroxyvitamin D compound and the active Vitamin D hormone. Co-treatment can be according to the disclosure hereinbelow, and can include co-administration and administration at different discrete intervals but overlapping in a term of periodic administration of the compounds. Co-administration includes concurrent administration, and is not limited to simultaneous administration. Co-treatment can include administration by the same or different routes of administration.

"Co-administration" means the administration of two or more compounds to the same patient. For example, co-administration encompasses (a) simultaneous administration of a first and second compound and (b) administration of a first compound, followed by administration of a second compound. For example, the first and second compounds can be administered within 24 hours, 8 hours, 4 hours, 2 hours, or 1 hour of each other. In other embodiments, different time periods of between administration of first and second compounds may be applicable.

"Suprapysiologic" in reference to intraluminal, intracellular and blood levels of Vitamin D refers to a total concentration of the vitamin D compound markedly greater than the generally stable levels observed in a Vitamin D-replete subject, animal or human patient over the course of any 24-hour period by laboratory measurement when Vitamin D supplementation has been withheld for at least 30 days. "Adverse suprapysiologic surge" refers to a local or serum concentration of a vitamin D compound that elicits adverse effects such as excessive extrarenal hormone production, leading to local adverse effects on calcium and phosphorus metabolism, inhibition of hepatic 25-hydroxylation of vitamin D, increased catabolism of both Vitamin D and 25-hydroxyvitamin D, hypercalciuria, hypercalcemia and/or hyperphosphatemia, with possible cardiovascular sequelae.

As used herein, the term "patient's normal historical physiological range of serum 1,25-dihydroxyvitamin D" refers to the average blood concentration range of 1,25-dihydroxyvitamin D of a patient based on at least two annual or biannual readings of serum 1,25-dihydroxyvitamin D levels taken while the kidneys are healthy.

As used herein the term "hypercalcemia" refers to condition in a patient wherein the patient has corrected serum levels of calcium above 10.2 mg/dL. Normal corrected serum levels of calcium for a human are between about 8.6 to 10.2 mg/dL.

As used herein, the term "hyperparathyroidism" refers to primary hyperparathyroidism, secondary hyperparathyroidism and hyperparathyroidism secondary to chronic kidney disease (Stage 3, 4 or 5).

The term "subject" as used herein generally includes humans, mammals (e.g., dogs, cats, rodents, sheep, horses, cows, goats), veterinary animals and zoo animals.

As used herein the term "hyperphosphatemia" refers to a condition in a patient having normal kidney function, or Stage 1-4 CKD, wherein the patient has serum phosphorous levels above 4.6 mg/dL. In a patient who has Stage 5 CKD, hyperphosphatemia occurs when the patient has serum levels above 5.5 mg/dL. Normal values for serum phosphorous in a human are 2.4-4.5 mg/dL.

As used herein the term "over suppression of plasma iPTH" refers to a condition in a patient having normal kidney function, or Stage 1-3 CKD, wherein the patient has levels of plasma iPTH below 15 pg/mL. In a patient having Stage 4 CKD, over suppression of plasma iPTH occurs when the patient has levels of plasma iPTH below 30 pg/mL. In a patient having Stage 5 CKD, over suppression of plasma iPTH occurs when the patient has levels of plasma iPTH below 100 pg/mL.

As used herein, the term "abnormally low bone turnover rate" refers to a condition in a patient wherein the rate of bone resorption is greater than the rate of bone formation.

As used herein, the term "Vitamin D repletion therapy" refers to the administration to a patient of an effective amount of a Vitamin D, a Vitamin D analog, a Vitamin D prohormone, and a Vitamin D prohormone analog. Particularly preferred are ergocalciferol, cholecalciferol, 25-hydroxyvitamin $D_2$, and 25-hydroxyvitamin $D_3$. The Vitamin D repletion therapy can be via any route of administration. In one preferred embodiment, the therapy will result in blood concentration of 25-hydroxyvitamin D comprising predominantly 25-hydroxyvitamin $D_3$. For example, in any of the methods described herein, the blood concentration of 25-hydroxyvitamin D will comprise greater than 50% 25-hydroxyvitamin $D_3$, or at least 60%, at least 70%, at least 80%, or at least 90% 25-hydroxyvitamin $D_3$. In another preferred embodiment, the therapy includes administering predominantly or solely 25-hydroxyvitamin $D_3$ for 25-hydroxyvitamin D repletion and/or maintenance. For example, in any of the methods described herein, the administration of 25-hydroxyvitamin D will comprise greater than 50% 25-hydroxyvitamin $D_3$, or at least 60%, at least 70%, at least 80%, at least 90%, or solely 25-hydroxyvitamin $D_3$.

As used herein, the term "Vitamin D hormone replacement therapy" refers to the administration to a patient of an effective amount of one or more of active vitamin D hormones, which include an active Vitamin D hormone metabolites, and active Vitamin D hormone analogs, such as 1α-hydroxylated Vitamin D compounds. Metabolites and analogs of Vitamin D which can substantially occupy the intracellular VDR or activate the VDR are preferred. 1,25-dihydroxyvitamin $D_2$, 1,25-dihydroxyvitamin $D_3$, 1,25-dihydroxyvitamin $D_4$, and analogs thereof are preferred.

As used herein, the term "controlled release" and "sustained release" are used interchangeably, and refer to the release of the administered vitamin D compound in a way that deviates from immediate release. The term "controlled release" optionally includes delayed release characteristics. For example, a delayed release type of controlled release formulation will be characterized by Cmax at a time greater than Cmax for an immediate release formulation. As another example, the release of an administered Vitamin D compound will preferably be at such a rate that total serum or blood levels of the Vitamin D compound are maintained or elevated above predosing levels for an extended period of time, e.g. 25-hydroxyvitamin D elevated for 4 to 24 hours or even longer. As another example, a sustained release type of controlled release formulation will be characterized by release at such a rate that total serum or blood levels of an active Vitamin D hormone are maintained or elevated above predosing levels for an extended period of time, e.g. 20 to 40 minutes, 1 to 15 hours or even longer.

In a method including controlled release of a Vitamin D compound (i.e. one or both of the compound(s) for Vitamin D repletion and active Vitamin D hormone replacement), the release rate of the vitamin D compound is controlled to reduce Cmax and/or delay Tmax and/or decrease $Cmax_{24 hr}/C_{24 hr}$ as described herein. Preferably both Cmax is reduced and Tmax is delayed (increased).

Thus, one embodiment includes a method of administering an amount of a vitamin D compound to a subject such that the maximum serum concentration of the vitamin D compound in a dose interval (Cmax) is reduced as compared to Cmax for an equivalent amount of a vitamin D compound administered by bolus IV injection and/or an equivalent immediate-release, oral dosage form. For example, the reduction is preferably by a factor of at least 50%, 60%, 70%, or 80%.

Another embodiment includes a method of administering an amount of a vitamin D compound to a subject such that the maximum change in serum concentration of a vitamin D compound in a dose interval is reduced as compared to an equivalent amount of a vitamin D compound administered by bolus IV injection and/or an equivalent immediate-release, oral dosage form. For example, the reduction is preferably by a factor of at least 50%, 60%, 70%, or 80%.

Still another embodiment includes a method of administering an amount of a vitamin D compound to a patient such that the ratio of the maximum serum concentration within 24 hours after administration of a vitamin D compound to the concentration 24 hours after administration ($Cmax_{24 hr}/C_{24 hr}$) is reduced as compared to an equivalent amount of a vitamin D compound administered by bolus IV injection and/or an equivalent immediate-release, oral dosage form. For example, the reduction is preferably by a factor of at least 50%, 60%, 70%, or 80%.

Yet another embodiment includes a method of administering an amount of a vitamin D compound to a subject such that the elimination half-life ($t_{1/2}$) of a vitamin D compound is increased as compared to $t_{1/2}$ for an equivalent amount of a vitamin D compound administered by bolus IV injection and/or an equivalent immediate-release, oral dosage form. For example, the increase is preferably by a factor of at least 25%, 30%, 40%, 50%, or 60%.

A further embodiment includes a method of administering an amount of a vitamin D compound to a subject such that the time for the plasma concentration of a vitamin D compound to reach its maximum in a dose interval following administration (Tmax) is increased as compared to Tmax for an equivalent amount of a vitamin D compound administered by bolus IV injection and/or an equivalent immediate-release, oral dosage form. For example, the increase is preferably by a factor of at least 25%, 30%, 40%, 50%, or 60%.

Furthermore, the compositions optionally can be designed for delayed release into the ileum of the gastrointestinal tract of humans or animals. It is contemplated that in one type of embodiment the compositions will ensure a substantially constant concentration of the desired Vitamin D compound in the body, and a more sustained blood level. By providing a slow and steady release over time, blood, intraluminal and intracellular concentration spikes, e.g., adverse supraphysiologic levels, are mitigated or eliminated.

Ergocalciferol, cholecalciferol, 25-hydroxyvitamin $D_2$ and/or 25-hydroxyvitamin $D_2$ 1,25-dihydroxyvitamin $D_3$, 1,25-dihydroxyvitamin $D_2$, 1,25-dihydroxyvitamin $D_4$, and other metabolites and analogs of Vitamin D are also useful as active compounds in pharmaceutical compositions. The pharmacologically active analogs of this invention can be processed in accordance with conventional methods of pharmacy to produce pharmaceutical agents for administration to patients, e.g., in admixtures with conventional excipients such as pharmaceutically acceptable organic or inorganic carrier substances suitable for parenteral, enteral (e.g., oral), topical or transdermal application which do not deleteriously react with the active compounds. Suitable pharmaceutically acceptable carriers include, but are not limited to, water, salt (buffer) solutions, alcohols, gum arabic, mineral and vegetable oils, benzyl alcohols, polyethylene glycols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc.

The pharmaceutical preparations can be sterilized and, if desired, mixed with auxiliary agents, e.g., lubricants, preservatives, stabilizers, wetting agents, emulsifiers, salts for influencing osmotic pressure, buffers, coloring, flavoring and/or aromatic active compounds. If a pharmaceutically acceptable solid carrier is used, the dosage form of the analogs may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form.

For parenteral application, particularly suitable are injectable, sterile solutions, preferably oily or aqueous solutions, as well as suspensions, emulsions, or implants, including suppositories. Ampoules are convenient unit dosages.

For enteral application, particularly suitable are tablets, dragees, liquids, drops, suppositories, or capsules such as soft gelatin capsules. A syrup, elixir, or the like can be used wherein a sweetened vehicle is employed.

Controlled release compositions can be formulated, e.g., liposomes or those wherein the active compound is protected with differentially degradable coatings, such as by microencapsulation, multiple coatings, etc. It is also possible to freeze-dry the new compounds and use the lyophilizates obtained, for example, for the preparation of products for injection. Transdermal delivery of pharmaceutical compositions of the compounds of the invention is also possible.

For topical application, there are employed as nonsprayable forms, viscous to semi-solid or solid forms comprising a carrier compatible with topical application and having a dynamic viscosity preferably greater than water. Suitable formulations include, but are not limited to, solutions, suspensions, emulsions, creams, ointments, powders, liniments, salves, aerosols, etc., which are, if desired, sterilized or mixed with auxiliary agents, e.g., preservatives, etc.

It is possible, if desired, to produce the metabolites of certain ones of the compounds of the invention, in particular by nonchemical means. For this purpose, it is possible to convert them into a suitable form for administration together with at least one vehicle or auxiliary and, where appropriate, combined with one or more other active compounds.

The dosage forms may also contain adjuvants, such as preserving or stabilizing adjuvants. They may also contain other therapeutically valuable substances or may contain more than one of the compounds specified herein and in the claims in admixture.

As described hereinbefore, Vitamin D repletion and Vitamin D hormone replacement therapies are preferably administered to the human patients in oral or intravenous dosage formulations. The administration of such therapies, in accordance with the present invention, can be on an episodic basis, suitably from daily, to 1 to 3 times a week. Suitably the dosage of Vitamin D repletion therapy or Vitamin D hormone replacement therapy is about 0.5 μg to about 400 μg per week, depending on the agent selected. Suitably such therapies can be given in a unit dosage form between about 0.5 μg to about 100 μg, or about 0.5 μg to about 10 μg in a pharmaceutically acceptable carrier per unit dosage. Episodic doses can be a single dose or, optionally, divided into 2-4 subdoses which, if desired, can be given, e.g., twenty minutes to an hour apart until the total dose is given.

The dosage of a 1,25-dihydroxyvitamin D for oral administration generally is about 0.1 μg per week to 100 μg per week, preferably about 0.7 μg per week to about 70 μg per week, which can be split into daily or other periodic doses, such as three times per week for administration concomitant with hemodialysis. In exemplary embodiments, an oral dosage equivalent to about 1, 2, 3, 4, 5, 6, 7, 8 or 9 μg per day is contemplated.

Generally, a 1,25-dihydroxyvitamin D compound can be dispensed by unit dosage form comprising about 0.1 μg to about 10 μg per unit dosage, for example about 1 μg to about 4 pg, about 2 μg to about 10 μg, or about 3 μg to about 5 μg.

The duration of the treatment is contemplated to be at least four weeks, or at least twelve weeks, and can be ongoing for years or even decades.

A controlled release composition intended for oral administration for Vitamin D repletion in accordance with the methods described herein preferably is designed to contain concentrations of the 25-hydroxyvitamin $D_3$, for example, of 1 to 100 μg per unit dose and are prepared in such a manner as to effect controlled or substantially constant release of the 25-hydroxyvitamin D, optionally into the ileum of the gastrointestinal tract, of humans or animals over an extended period of time. The compositions and methods may provide substantially increased absorption of 25-hydroxyvitamin D via transport on DBP and decreased absorption via transport in chylomicrons. The compositions and methods may provide maintenance of substantially constant blood levels of 25-hydroxyvitamin D during the 24-hour post-dosing period. By providing both a gradual, sustained and direct release of the 25-hydroxyvitamin D and absorption preferentially to circulating DBP (rather than to chylomicrons), blood, intraluminal and intracellular 25-hydroxyvitamin D concentration spikes, i.e., supraphysiologic levels and related unwanted catabolism can be mitigated or eliminated.

Advantageously, the compound, such as 25-hydroxyvitamin $D_3$, together with other therapeutic agents can be orally or intravenously administered in accordance with the above described embodiments in dosage amounts of from 1 to 100 μg per day, with the preferred dosage amounts of from 5 to 50 μg per day, for example about 10 to 25 μg. Preferred doses will provide an average rise in serum 25-hydroxyvitamin $D_3$ of about 1 to 3 ng/mL.

In embodiments, the method is contemplated to include administering a formulation described herein to raise and preferably also maintain blood 1,25-dihydroxyvitamin D levels at 25 pg/mL, 30 pg/mL, or higher, e.g. 25-65 pg/mL for an extended period, for example at least one month, at least three months, at least six months, or longer.

Those of ordinary skill in the art will readily optimize effective doses and co-administration regimens as determined by good medical practice and the clinical condition of the individual patient. Regardless of the manner of administration, it will be appreciated that the actual preferred amounts of active compound in a specific case will vary according to the efficacy of the specific compound employed, the particular compositions formulated, the mode of application, and the particular situs and organism being treated. For example, the specific dose for a particular patient depends on age, sex, body weight, general state of health, on diet, on the timing and mode of administration, on the rate of excretion, and on medicaments used in combination and the severity of the particular disorder to which the therapy is applied. Dosages for a given patient can be determined using conventional considerations, e.g., by customary comparison of the differential activities of the subject compounds and of a known agent, such as by means of an appropriate conventional pharmacological protocol. A physician of ordinary skill can readily determine and prescribe the effective amount of the drug required to counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug. The dosage of active ingredient in the compositions of this invention may be varied; however, it is necessary that the amount of the active ingredient be such that an efficacious dosage is obtained. The active ingredient is administered to patients (animal and human) in need of treatment in dosages that will provide optimal pharmaceutical efficacy.

Bulk quantities of Vitamin D and Vitamin D analogs in accordance with the present invention can be readily obtained in accordance with the many widely known processes.

The present invention is further explained by the following examples which should not be construed by way of limiting the scope of the present invention. The following examples demonstrate that the concomitant administration of Vitamin D repletion and Vitamin D hormone replacement therapies has improved efficacy in reducing or preventing elevated blood PTH levels as well as maintaining adequate and appropriate levels of serum calcium, serum phosphorous, serum total 25-hydroxyvitamin D and serum total 1,25-dihydroxyvitamin D.

EXAMPLES

The following examples are provided for illustration and are not intended to limit the scope of the invention.

Example 1: Efficacy Study in Adult Patients with CKD and Secondary Hyperparathyroidism The effectiveness of three different Vitamin D treatment regimens in controlling elevated serum iPTH is examined in a 26-week study of non-obese patients diagnosed with secondary hyperparathyroidism and CKD. Two formulations containing Vitamin D are prepared. One of the formulations (Formulation #1) is a soft gelatin capsule containing 5,000 IU of Vitamin D, comprised of a mixture of 2,500 IU of cholecalciferol and 2,500 IU of ergocalciferol and prepared in a delayed sustained release formulation. The second formulation (Formulation #2) is soft gelatin capsule of identical appearance containing 0.5 mcg of 1,25-dihydroxyvitamin $D_2$ prepared in a delayed sustained release formulation. A total of 100 Caucasian and African-American patients participate in this study, all of whom are aged 30 to 70 years, have Stage 4 CKD, exhibit serum calcium levels between 8.6 and 10.2 mg/dL (inclusive), exhibit serum phosphorus levels below 4.5 mg/dL, have serum total 25-hydroxyvitamin D levels between 5 and 15 ng/mL (inclusive), have serum total 1,25-dihydroxyvitamin D between 5 and 15 pg/mL (inclusive), and have plasma iPTH above 250 pg/mL. All subjects abstain from taking Vitamin D therapies of any kind for 60 days before study start and, except for the test formulations, continuing through study termination. On Day 1 and 2 of the study, all subjects provide fasting morning blood samples to establish pre-treatment baseline values of serum total 25-hydroxyvitamin D, serum total 1,25-dihydroxyvitamin D, plasma iPTH, serum calcium and serum phosphorus. On the morning of Day 3, the subjects provide an additional fasting blood sample (t=0), are randomly assigned to one of four treatment groups, and are dosed daily for 26 weeks prior to eating breakfast: the subjects in Group #1 each receive a single capsule of Formulation #1; the subjects in Group #2 each receive a single capsule of Formulation #2; the subjects in Group #3 each receive a single capsule of Formulation #1 plus a single capsule of Formulation #2; and, subjects in Group #4 receive a matching placebo capsule. A fasting morning blood sample is drawn from each subject, irrespective of treatment group, at weekly intervals just prior to dosing. All collected blood is analyzed for the contained levels of 25-hydroxyvitamin D, 1,25-dihydroxyvitamin D, plasma iPTH, serum calcium and serum phosphorus, and the data are analyzed by treatment group. Subjects in all four treatment groups exhibit mean baseline serum total 25-hydroxyvitamin D levels of approximately 8-11 ng/mL, based on analysis of fasting blood samples drawn on Days 1 through 3. Subjects in Group #4 (control group) show no significant changes in any of the parameters measured over the course of the study. Subjects in Group #1 show during treatment a steadily increasing mean serum 25-hydroxyvitamin D reaching approximately 34 ng/mL, a significant reduction in plasma iPTH, and no significant changes in the other measured parameters. Subjects in Group #2 show a significant increase in serum total 1,25-dihydroxyvitamin D, a significant decrease in iPTH, slightly increasing trends in serum calcium and serum phosphorus, and no significant changes in mean serum 25-hydroxyvitamin D. Subjects in Group #3 exhibit the same changes observed in Group #2 except that (a) the decrease in iPTH over the course of the treatment period is significantly greater by study end than in Groups #1 and #2, and (b) serum total 25-hydroxyvitamin D show steadily increasing mean serum 25-hydroxyvitamin D reaching approximately 36 ng/mL by Week 26. The data from this study demonstrate that administration of both Vitamin D repletion therapy and Vitamin D hormone replacement therapy is substantially more effective in controlling secondary hyperparathyroidism and normalizing serum total levels of both 25-hydroxyvitamin D and 1,25-dihydroxyvitamin D without causing unwanted aberrations in serum calcium and serum phosphorus in patients with CKD Stage 4.

Example 2: Efficacy Study in Adult Patients with CKD and Secondary Hyperparathyroidism The effectiveness of three different Vitamin D treatment regimens in controlling elevated serum iPTH is examined in a 26-week study of non-obese patients diagnosed with secondary hyperparathyroidism and CKD. Two formulations containing Vitamin D are prepared. One of the formulations (Formulation #1) is a soft gelatin capsule containing 5,000 IU of Vitamin D, comprised of a mixture of 4,000 IU of cholecalciferol and 1,000 IU of ergocalciferol and prepared in a delayed sustained release formulation. The second formulation (Formulation #2) is soft gelatin capsule of identical appearance containing 0.5 mcg of 1,25-dihydroxyvitamin $D_2$ prepared in a delayed sustained release formulation. A total of 100 Caucasian and African-American patients participate in this study, all of whom are aged 30 to 70 years, have Stage 4 CKD, exhibit serum calcium levels between 8.6 and 10.2 mg/dL (inclusive), exhibit serum phosphorus levels below 4.5 mg/dL, have serum total 25-hydroxyvitamin D levels between 5 and 15 ng/mL (inclusive), have serum total 1,25-dihydroxyvitamin D between 5 and 15 pg/mL (inclusive), and have plasma iPTH above 250 pg/mL. All subjects abstain from taking Vitamin D therapies of any kind for 60 days before study start and, except for the test formulations, continuing through study termination. On Day 1 and 2 of the study, all subjects provide fasting morning blood samples to establish pre-treatment baseline values of serum total 25-hydroxyvitamin D, serum total 1,25-dihydroxyvitamin D, plasma iPTH, serum calcium and serum phosphorus. On the morning of Day 3, the subjects provide an additional fasting blood sample (t=0), are randomly assigned to one of four treatment groups, and are dosed daily for 26 weeks prior to eating breakfast: the subjects in Group #1 each receive a single capsule of Formulation #1; the subjects in Group #2 each receive a single capsule of Formulation #2; the subjects in Group #3 each receive a single capsule of Formulation #1 plus a single capsule of Formulation #2; and, subjects in Group #4 receive a matching placebo capsule. A fasting morning blood sample is drawn from each subject, irrespective of treatment group, at weekly intervals just prior to dosing. All collected blood is analyzed for the contained levels of 25-hydroxyvitamin D, 1,25-dihydroxyvitamin D, plasma iPTH, serum calcium and serum phosphorus, and the data are analyzed by treatment group. Subjects in all four treatment groups exhibit mean baseline serum total 25-hydroxyvitamin D levels of approximately 8-11 ng/mL, based on analysis of fasting blood samples drawn on Days 1 through 3. Subjects in Group #4 (control group) show no significant changes in any of the parameters measured over the course of the study. Subjects in Group #1 show during treatment a significant increase in mean serum 25-hydroxyvitamin D (with the predominant species being 25-hydroxyvitamin $D_3$), a significant reduction in plasma iPTH, and no significant changes in the other measured parameters. Subjects in Group #2 show a significant increase in serum total 1,25-dihydroxyvitamin D, a significant decrease in iPTH, slightly increasing trends in serum calcium and serum phosphorus, and no significant changes in mean serum 25-hydroxyvitamin D. Subjects in Group #3 exhibit the same changes observed in Group #2 except that (a) the decrease in iPTH over the course of the treatment period is significantly greater by study end than in Groups #1 and #2, and (b) serum total 25-hydroxyvitamin D show significantly increased mean serum 25-hydroxyvitamin D by Week 26. The data from this study demonstrate that administration of both Vitamin D repletion therapy and Vitamin D hormone replacement therapy is substantially more effective in controlling secondary hyperparathyroidism and normalizing serum total levels of both 25-hydroxyvitamin D and 1,25-dihydroxyvitamin D without causing unwanted aberrations in serum calcium and serum phosphorus in patients with CKD Stage 4.

While the present invention has now been described and exemplified with some specificity, those skilled in the art will appreciate the various modifications, including variations, additions, and omissions that may be made in what has been described. Accordingly, it is intended that these modifications also be encompassed by the present invention and that the scope of the present invention be limited solely by the broadest interpretation that lawfully can be accorded the appended claims.

All patents, publications and references cited herein are hereby fully incorporated by reference. In case of conflict between the present disclosure and incorporated patents, publications and references, the present disclosure should control.

Embodiments contemplated in view of the foregoing description include the following numbered paragraphs.

1. A method of increasing or maintaining blood concentrations of both 25-hydroxyvitamin D and 1,25-dihydroxyvitamin D in a human patient, including administering both Vitamin D repletion and Vitamin D hormone replacement therapies, wherein the blood concentrations of 25-hydroxyvitamin D are increased to and maintained at or above 30 ng/mL, and blood concentrations of 1,25-dihydroxyvitamin D are increased to or maintained within a patient's normal historical physiological range for 1,25-dihydroxyvitamin D.

2. A method of concurrently lowering or maintaining plasma iPTH levels, increasing or maintaining serum calcium levels, maintaining serum phosphorous levels, increasing or maintaining serum 25-hydroxyvitamin D, and increasing or maintaining serum 1,25-dihydroxyvitamin D levels in a human patient by administering to the patient both Vitamin D repletion and Vitamin D hormone replacement therapies.

3. A method of reducing the risk of over suppression of plasma iPTH levels in a patient undergoing treatment for elevated levels of plasma iPTH, including administering both Vitamin D repletion and Vitamin D hormone replacement therapies in amounts sufficient to decrease elevated plasma iPTH levels while avoiding an abnormally low bone turnover rate.

4. A method of maintaining in a patient blood concentrations of 25-hydroxyvitamin D at or above 30 ng/mL and blood concentrations of 1,25-dihydroxyvitamin D in a patient at levels within the patient's normal historical physiological range while lowering elevated blood levels if iPTH without causing substantially increased risk of hypercalcemia, hyperphosphatemia or over suppression of plasma iPTH including administering to the patient an effective amount, as needed, of both a Vitamin D repletion therapy and a Vitamin D hormone replacement therapy.

5. The method according to any one of the preceding paragraphs, wherein the blood levels of 25-hydroxyvitamin D are maintained at or above 30 ng/mL between doses of Vitamin D repletion therapies, and the blood levels of 1,25-dihydroxyvitamin D are maintained in the patient's normal historical physiological range between doses of Vitamin D hormone replacement therapies.

6. The method according to any one of the preceding paragraphs, wherein the blood concentration of 25-hydroxyvitamin D during treatment includes predominantly 25-hydroxyvitamin $D_3$.

7. The method according to any one of the preceding paragraphs, wherein the administering of Vitamin D repletion includes administering predominantly 25-hydroxyvitamin $D_3$.

8. The method according to any one of the preceding paragraphs, wherein the administering of Vitamin D repletion therapy includes controllably releasing a compound for Vitamin D repletion.

9. The method according to any one of the preceding paragraphs, wherein the administering of Vitamin D hormone replacement therapy includes controllably releasing a compound for Vitamin D hormone replacement.

10. The method according to any one of the preceding paragraphs, wherein the patient suffers from chronic kidney disease.

11. The method of paragraph 10, wherein the chronic kidney disease is Stage 1, Stage 2, Stage 3, or Stage 4.

12. The method of paragraph 10, wherein the chronic kidney disease is Stage 3, Stage 4, or Stage 5.

13. The method of paragraph 12, wherein the chronic kidney disease is Stage 3 or Stage 4.

14. The method of paragraph 12, wherein the chronic kidney disease is Stage 5.

15. The method according to any one of the preceding paragraphs, further including co-treatment with a phosphate binder.

16. The method according to any one of the preceding paragraphs, further including co-treatment with a calcimimetic agent.

17. The method according to paragraph 2, wherein the administering of Vitamin D repletion comprises administering predominantly 25-hydroxyvitamin $D_3$.

18. The method according to paragraph 3, wherein the administering of Vitamin D repletion comprises administering predominantly 25-hydroxyvitamin $D_3$.

19. The method according to paragraph 4, wherein the administering of Vitamin D repletion comprises administering predominantly 25-hydroxyvitamin $D_3$.

20. The method according to paragraph 2, wherein the patient suffers from chronic kidney disease.

What is claimed is:

1. A method of treating hyperparathyroidism secondary to chronic kidney disease by increasing or maintaining blood concentrations of both 25-hydroxyvitamin D and 1,25-dihydroxyvitamin D in a patient by administering a 25-hydroxyvitamin D compound by transdermal delivery.

2. The method of claim 1, wherein the administration is by application of a topical preparation.

3. The method of claim 2, wherein the topical preparation has a dynamic viscosity greater than water.

4. The method of claim 2, wherein the topical preparation is selected from a suspension, and emulsion, a cream, an ointment, a liniment, and a salve.

5. The method of claim 2, wherein the preparation further comprises one or more excipients selected from a liquid carrier, a lubricant, a preservative, a stabilizer, a wetting agent, an emulsifier, a salt for influencing osmotic pressure, a buffer, a coloring, and an aromatic active compound.

6. The method of claim 2, wherein the topical preparation comprises a transdermal patch.

7. The method of claim 5, wherein the topical preparation comprises a transdermal patch.

8. The method of claim 2, wherein the topical preparation comprises the 25-hydroxyvitamin D present in an amount in a range of 1 µg to 1000 µg.

9. The method of claim 1, wherein the administration is at a dosage of about 0.5 µg to about 400 µg per week.

10. The method of claim 1, wherein the treatment increases the patient's serum total 25-hydroxyvitamin D level to at least 30 ng/mL.

11. The method of claim 1, wherein the treatment lowers the patient's serum iPTH level.

12. The method of claim 11, wherein the treatment lowers the patient's serum iPTH level by at least 30%.

13. The method of claim 11, wherein the treatment lowers the patient's serum iPTH level to a target range of 35-70 pg/mL if the patient suffers from Stage 3 Chronic Kidney Disease, or a target range of 70-110 pg/mL if the patient suffers from Stage 4 Chronic Kidney Disease, or a target range of 150-300 pg/mL if the patient suffers from Stage 5 Chronic Kidney Disease.

14. The method of claim 1, wherein the 25-hydroxyvitamin D compound comprises 25-hydroxyvitamin $D_3$.

15. The method of claim 1, wherein the treatment further comprises administration of a second agent selected from phosphate binders and calcimimetic agents.

16. The method of claim 1, wherein the treatment further comprises administration of a 1α-hydroxylated Vitamin D compound.

17. The method of claim 16, wherein the 1α-hydroxylated Vitamin D compound is selected from one or more compounds in the group of 1,25-dihydroxyvitamin $D_2$, 1,25-dihydroxyvitamin $D_3$, and 1,25-dihydroxyvitamin $D_4$.

18. The method of claim 1, wherein the patient has Stage 3 or Stage 4 Chronic Kidney Disease.

19. A method of treating hyperparathyroidism secondary to chronic kidney disease in a patient by administering to the patient a 25-hydroxyvitamin D compound by transdermal delivery, whereby the patient's serum total 25-hydroxyvitamin D level is raised to at least 30 ng/mL and the patient's serum iPTH is lowered.

20. A method of treating hyperparathyroidism secondary to chronic kidney disease in a patient by administering to the patient 25-hydroxyvitamin $D_3$ by transdermal delivery, whereby the patient's serum total 25-hydroxyvitamin D level is raised to at least 30 ng/mL and the patient's serum iPTH is lowered, and wherein the delivery is by transdermal patch having a concentration of the 25-hydroxyvitamin $D_3$ in a range of 1 µg to 1000 µg.

* * * * *

UNITED STATES PATENT AND TRADEMARK OFFICE
CERTIFICATE OF CORRECTION

| | |
|---|---|
| PATENT NO. | : 11,452,734 B2 |
| APPLICATION NO. | : 16/858395 |
| DATED | : September 27, 2022 |
| INVENTOR(S) | : Charles W. Bishop et al. |

It is certified that error appears in the above-identified patent and that said Letters Patent is hereby corrected as shown below:

In the Claims

At Column 18, Line 61, in Claim 4, "and" should be -- an --.

Signed and Sealed this
Eleventh Day of April, 2023

Katherine Kelly Vidal
*Director of the United States Patent and Trademark Office*